United States Patent
Redel

(10) Patent No.: US 10,828,109 B2
(45) Date of Patent: Nov. 10, 2020

(54) TREATMENT PLANNING FOR A STENOSIS IN A VASCULAR SEGMENT BASED ON VIRTUAL HEMODYNAMIC ANALYSIS

(71) Applicant: Thomas Redel, Poxdorf (DE)

(72) Inventor: Thomas Redel, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 420 days.

(21) Appl. No.: 15/809,473

(22) Filed: Nov. 10, 2017

(65) Prior Publication Data
US 2018/0125583 A1    May 10, 2018

(30) Foreign Application Priority Data

Nov. 10, 2016    (DE) .................. 10 2016 222 102

(51) Int. Cl.
*A61B 34/10*    (2016.01)
*G16H 20/40*    (2018.01)
(Continued)

(52) U.S. Cl.
CPC .............. *A61B 34/10* (2016.02); *A61B 6/504* (2013.01); *A61B 6/507* (2013.01); *A61B 6/5217* (2013.01);
(Continued)

(58) Field of Classification Search
CPC ......... A61B 34/10; A61B 6/504; A61B 6/507; A61B 6/5217; A61B 6/5241;
(Continued)

(56) References Cited

U.S. PATENT DOCUMENTS 8,157,742 B2    4/2012    Taylor
9,974,453 B2 *  5/2018    Fonte .................. A61B 6/032
(Continued)

FOREIGN PATENT DOCUMENTS

DE    102014210591 A1    12/2015
DE    202014010680 U1    6/2016
(Continued)

OTHER PUBLICATIONS

Michael Broome et. al., Closed-loop real-time simulation model of hemodynamics and oxygen transport in the cardiovascular system, BioMed Central Ltd., pp. 1-20, 2013 (Year: 2013).*
(Continued)

*Primary Examiner* — Justin C Mikowski
(74) *Attorney, Agent, or Firm* — Lempia Summerfield Katz LLC

(57) ABSTRACT

A method for planning treatment of a stenosis in a vascular segment includes providing a geometric description of the vascular segment on a computer and determining a course of a hemodynamic parameter of the vascular segment along the vascular segment based on the geometric description provided by the computer. The computer calculates a mathematical derivative of the hemodynamic parameter over the length of the vascular segment along the vascular segment. At least one length section is specified for the vascular segment, and a value of the hemodynamic parameter in a distal end region of the vascular segment is simulated for a treatment device introduced virtually into the specified length section as a function of the mathematical derivative. The treatment of the stenosis including the introduction of the treatment device into the specified length section is planned as a function of the simulated value for the hemodynamic parameter.

19 Claims, 5 Drawing Sheets

(51) Int. Cl.
*G16H 30/40* (2018.01)
*A61B 6/00* (2006.01)
*G16H 50/50* (2018.01)
*A61B 90/00* (2016.01)
*A61B 8/06* (2006.01)
*A61B 8/08* (2006.01)

(52) U.S. Cl.
CPC .......... *A61B 6/5241* (2013.01); *G16H 20/40* (2018.01); *G16H 30/40* (2018.01); *G16H 50/50* (2018.01); *A61B 6/5247* (2013.01); *A61B 8/06* (2013.01); *A61B 8/488* (2013.01); *A61B 2034/104* (2016.02); *A61B 2034/105* (2016.02); *A61B 2090/367* (2016.02); *A61B 2090/376* (2016.02)

(58) Field of Classification Search
CPC ........ A61B 2034/104; A61B 2034/105; A61B 2090/367; A61B 2090/376; A61B 6/5247; A61B 8/06; A61B 8/488; G16H 20/40; G16H 50/50; G16H 30/40
USPC .............................................................. 703/2
See application file for complete search history.

(56) References Cited

U.S. PATENT DOCUMENTS

| | | | | |
|---|---|---|---|---|
| 10,398,386 | B2* | 9/2019 | Grady | A61B 5/021 |
| 2003/0083582 | A1* | 5/2003 | Hirsh | A61B 5/02028 |
| | | | | 600/509 |
| 2012/0084064 | A1* | 4/2012 | Dzenis | G16H 50/50 |
| | | | | 703/11 |
| 2014/0372096 | A1 | 12/2014 | Spilker et al. | |
| 2015/0038860 | A1* | 2/2015 | Fonte | A61B 6/50 |
| | | | | 600/505 |
| 2015/0051885 | A1* | 2/2015 | Grady | G16H 50/50 |
| | | | | 703/2 |
| 2015/0356753 | A1 | 12/2015 | Lauritsch et al. | |
| 2016/0148372 | A1 | 5/2016 | Itu et al. | |
| 2017/0258431 | A1* | 9/2017 | Klingenbeck | A61B 6/504 |
| 2018/0325388 | A1* | 11/2018 | Lavi | A61B 6/5217 |
| 2018/0344173 | A1* | 12/2018 | Tu | A61B 5/026 |

FOREIGN PATENT DOCUMENTS

| | | |
|---|---|---|
| EP | 2665043 A1 | 11/2013 |
| WO | 2015153362 A1 | 10/2015 |

OTHER PUBLICATIONS

Oh-young Song et. al., Derivative Particles for Simulating Detailed Movements of Fluids, IEEE Transactions on Visualization and Computer Graphics, vol. 13, No. 4, Jul./Aug. 2007 (Year: 2007).*
De Bruyne, B., and J. Sarma. "Fractional flow reserve: a review." Heart 94.7 (2008): 949-959.
German Office Action for German Application No. 102016222102.7, dated Aug. 23, 2017.
Morris, Paul D., et al. ""Virtual"(computed) fractional flow reserve: current challenges and limitations." JACC: Cardiovascular Interventions 8.8 (2015): 1009-1017.
Nijjer, Sukhjinder S., et al. "The Instantaneous wave-Free Ratio (iFR) pullback: a novel innovation using baseline physiology to optimise coronary angioplasty in tandem lesions." Cardiovascular Revascularization Medicine 16.3 (2015): 167-171.

* cited by examiner

TREATMENT PLANNING FOR A STENOSIS IN A VASCULAR SEGMENT BASED ON VIRTUAL HEMODYNAMIC ANALYSIS

This application claims the benefit of DE 10 2016 222 102.7, filed on Nov. 10, 2016, which is hereby incorporated by reference in its entirety.

BACKGROUND

The present embodiments relate to planning treatment of at least one stenosis in a vascular segment.

Stenoses (e.g., narrowings of vessels such as blood vessels; stenoses of the cardiac valves or coronary vessels) are one of the diseases counted as the greatest cost drivers in health care. In order to decide whether a stenosis should be treated or not, a value for the fractional flow reserve (FFR value), an index value for the condition of the vessel, is calculated. For the calculation of the FFR value, typically during cardiac catheterization, the proximal pressure is measured in an artery before the stenosis and the distal pressure is measured in the artery after the stenosis. The distal pressure is divided by the proximal pressure in order to arrive at the FFR value. Prior to the measurement of the corresponding pressures, a drug (e.g., adenosine) is administered in order to induce hyperemia. If the FFR value is below a specified limit value, it is assumed that the patient will benefit from the implantation of a vascular support (e.g., a stent).

I many cases, a vascular segment contains not one single, clearly defined and demarcated stenosis, but more than one stenosis or a diffuse stenosis, which is not clearly demarcated from its environment. In such cases, at present, an attempt is made to implant as few stents as possible and at the same time to keep the stents as short as possible. This is due to the fact that stents may give rise to a stenosis or other unwanted effects such as, for example, restenosis (e.g., a new narrowing) and are associated with additional costs and risks during implantation.

This gives rise to the problem that, when planning treatment for the stenosis, a decision is to be made as to which stenosis should be treated in order to establish sufficient flow through the vascular segment and/or to adapt the length of a stent so as to achieve an optimum result with the lowest possible number of stents and the shortest possible overall length of the stents.

"Fractional Flow Reserve: A Review," by B. De Bruyne and J. Sarma in Heart 2008, Volume 94, pp 949-959 discloses that the best method for quantitative hemodynamic analysis of a stenosis is fractional flow reserve analysis, with which an FFR value is measured with a pressure wire. This FFR analysis is only correct when the entire stenotic region of the vascular segment, which may also include separate stenoses, is measured. It is not possible to quantify the individual stenoses in a series of sequential stenoses since, in the case of hyperemia, every stenosis influences the entire blood flow in the vascular segment. It is, therefore, very cumbersome and impractical to consider one stenosis in isolation during the above-described FFR analysis. However, slow withdrawal (e.g., pullback) of the pressure wire enables the position and the physiological significance of sequential stenoses to be determined even in the case of hyperemia. A visual inspection of a pressure drop or a comparison of the different pressure drops in the individual stenoses may be used as an indication of the appropriate treatment.

The drawbacks are partially avoided by an analytical method based on an instantaneous wave-free pressure ratio (e.g., "instantaneous wave free ratio, iFR"). This is described in an article by Sukhjinder S. Nijjer et al., "The Instantaneous wave-Free Ratio (iFR) pullback: a novel innovation using baseline physiology to optimise coronary angioplasty in tandem lesions," in Cardiovascular Revascularization Medicine 2015, Volume 16, pp 167-171. Herein, no adenosine is administered since the method described does not require hyperemia. This keeps the flow through the vascular segment constant during treatment of a stenosis. This enables prognostic planning of the treatment. This method, however, still requires a pressure wire that is to be introduced into the patient invasively.

However, there are also new, virtual methods, by which an FFR value may be calculated purely with image data and computational methods. This has the advantage that the FFR value may be determined in a first estimation without having to perform invasive proximal and distal pressure measurements with a catheter in the relevant vessel or vascular segment. This does not require the administration of drugs since, in addition, hyperemia is not necessary. A major advantage of the virtual method is that it is possible to model different situations, which may not be easily tested in reality. It is known from the article by Paul Morris et al., "Virtual (Computed) Fractional Flow Reserve," in Cardiovascular Interventions 2015, Volume 8, No 8, pp 1009-1017 how to model a treatment virtually (e.g., how to perform virtual treatment). For example, this enables the virtual (e.g., simulated) implantation of a stent in a vascular segment (e.g., the implantation of a virtual stent) and the subsequent virtual calculation of an FFR value, a virtual FFR value. During the virtual method (e.g., during the simulation), a first stenosis may be treated virtually, and the corresponding subsequent total FFR value may be calculated. After this, a second stenosis may be treated virtually, and the resulting total FFR value may be calculated again and so forth. This again enables some of the drawbacks described to be overcome. The drawback of this approach is the fact that it is necessary to perform a plurality of virtual stent implantations together with a plurality of FFR value calculations, which takes time and ties up computing capacity. It is, in each case, necessary to adapt the model on which the FFR values calculations are based in a computing-intensive procedure.

A system for planning treatment for a patient is also known from U.S. Pat. No. 8,157,742 B2. With this system, a three-dimensional model is used to calculate an FFR value for an anatomical structure, and the corresponding three-dimensional model is modified in order then to calculate a further FFR value for the anatomical structure for the modified three-dimensional model.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method and an appliance that enable quick and simple treatment of single, multiple, or diffuse stenoses without the need for invasive measurement of a hemodynamic parameter are provided.

One or more of the present embodiments are based on the assumption that the flow through a vascular segment (e.g., a segment of a coronary vessel segment) is the same before and after simulated (e.g., virtual) treatment. In a normal condition of the vessel (e.g., a condition without hyperemia), the blood flow is regulated by the myocardial tissue in accordance with the physiological need. Therefore, the assumption of a constant flow makes sense when one or more stenoses are to be removed or compensated by the treatment. Hence, the assumption of a constant flow before and after treatment is based on a physiological fact.

The assumption applies, for example, to small and medium stenoses. In very greatly pronounced stenoses, the assumption may result in an error since a correspondingly pronounced pressure drop may cause turbulence to form in the flow pattern on the distal side of the stenosis (e.g., downstream in a blood flow behind the stenosis). However, such strongly pronounced stenoses, which greatly influence the blood flow, are already treated even without virtual planning or virtual treatment. However, despite the limitation, for pronounced stenoses, it is also possible, similar to the case with the iFR method, to take account of turbulence caused by the strongly pronounced stenosis in a simulation (e.g., virtual analysis) and to integrate this in the calculated pressure drop across the actual stenosis. This assumption also makes sense since the turbulence downstream of the stenosis will also disappear following treatment of the strongly pronounced stenosis.

One or more of the present embodiments relate to a method for planning treatment of a stenosis in a vascular segment of a body. The method may also include further method acts, and so, one or more of the present embodiments may include a method for monitoring treatment of a stenosis or therapy guidance for treating a stenosis. The treatment of the stenosis may, for example, include treatment of a stenosis in a vascular segment with a diffuse stenosis and/or a plurality of serial stenoses. The vascular segment may be a section of a vessel through which blood flows from a proximal end of the vascular segment to a distal end of the vascular segment in a main direction of flow of the vascular segment. For example, such a vessel can include a coronary vessel, such as a right coronary artery, a left coronary artery, or a corresponding partial segment of the vessels.

In a first method act, a geometric description of the vascular segment (e.g., a three-dimensional model of the vascular segment) is provided to a computing device. For example, the geometric description may be a three-dimensional geometric description. The geometric description may include a 2D-model or at least two 2D models of the vascular segment that are, for example, registered to one another. The geometric description may, for example, include the three-dimensional model or an equivalent description with a number of geometric properties known to be relevant for the further calculations. This may, for example, be performed by an imaging medical apparatus (e.g., a fluoroscopic apparatus). However, the imaging medical apparatus may also be a computed tomography scanner and/or a magnetic resonance scanner and/or an ultrasound apparatus and/or an angiography apparatus. For example, the medical apparatus may be part of a catheter laboratory. This is advantageous since nowadays a patient with a diseased coronary vessel or another diseased blood vessel is given an imaging examination to provide three-dimensional image information. This provides that, regardless of the precise diagnosis, typically, three-dimensional image information for the corresponding vessel, and hence the vascular segment, is available. The three-dimensional image information may include both a symbolic reconstruction of, for example, two two-dimensional angiograms and also more complex images with dynamic trajectories. These three-dimensional reconstructions or items of image information may be used to calculate the geometric description provided (e.g., the three-dimensional model provided), for example, by segmentation of the corresponding image data. This geometric description (e.g., the three-dimensional model) may then be used for the corresponding calculation of a hemodynamic parameter. Alternatively or supplementarily, features of the geometry of the vascular segment may be derived from the three-dimensional reconstruction and/or the three-dimensional image information and/or the two-dimensional images or source images.

A further method act is accordingly determination of a course of a hemodynamic parameter s of the vascular segment along the vascular segment based on the geometric description provided (e.g., the model provided by the computing device). The hemodynamic parameter s may be a virtual hemodynamic parameter s. A virtual parameter may be a theoretically calculated parameter (e.g., a parameter) that is not itself measured or is not only calculated from measured variables. For example, this may be performed with an estimation or calculation of a blood flow through the vessel based on the geometric description provided (e.g., the model provided by the computing device). Herein, the blood flow through the vascular segment may, for example, be estimated according to Murray's law, according to which a flow is proportional to a radius of the vessel $r^n$, or from the myocardial mass. Alternatively or supplementarily, the blood flow may be calculated based on measurements such as time-density curves or contrast medium transport in one or more conditions. Herein, the front of the contrast medium bolus in the vascular segment is determined at at least two time points, and after measuring the path difference, the velocity of the front is calculated. Together with knowledge of the cross section of a valve, this may be converted into a blood flow. Where possible, information on the blood flow may be obtained based on a measurement (e.g., from the ultrasonic Doppler effect).

Different techniques such as computer-based fluid dynamics or machine learning may be employed to use the calculated or estimated blood flow to determine a change in the at least one hemodynamic parameter (e.g., one or more hemodynamic parameters along the vascular segment with one or more stenoses) and hence the course of the hemodynamic parameter (e.g., a theoretically calculated or virtual hemodynamic parameter; the course of a virtual FFR value along the vascular segment). The hemodynamic parameter s may, for example, be determined along a middle line or centerline of the vascular segment.

A next method act is calculation of a mathematical derivative $c=ds/dl$ of the hemodynamic parameter s over the length l of the vascular segment along the vascular segment by the computing device. For example, the mathematical derivative c may describe the local change in the hemodynamic parameter s between a proximal end region of the vascular segment and a distal end region of the vascular segment at a in each case determined by the value $c(l)$ of the mathematical derivative at the position determined by l. Herein, the proximal end region is arranged in a flow through the vascular segment upstream of the distal end region. The corresponding curve of the derivative c over the length l may, for example, be used in order qualitatively to evaluate an individual contribution of one or more respective stenoses to the change in the hemodynamic parameter (e.g., the drop in the hemodynamic parameter s) along the vascular segment. As explained in more detail below, the course of the mathematical derivative $c(l)$ along the vascular segment (e.g., a curve depicting the mathematical derivative c over the length l) may also be used to quantify treatment outcome and to plan the treatment accordingly.

Accordingly, a further method act is specification in the sense of a selection of at least one length section for the vascular segment (e.g., by the selection of a corresponding curve section between two positions on the l-axis over which the mathematical derivative c may be depicted). The specification may be used to select a length section for the vascular segment for which introduction of a treatment device is to be planned (e.g., implantation of a vascular support, also known as a stent). A length section in which the amount of the value of the mathematical derivative c is greater than the value is in the environment of the length section may, for example, be selected. For example, the specification may also be made by the computing device.

This is followed as a further method act by simulation of a value of the hemodynamic parameter s in a distal end region or end of the vascular segment for a treatment device introduced virtually into the specified length section (e.g., a virtual treatment device) as a function of the mathematical derivative c. Herein, a treatment device may be a treatment appliance such as, for example, a vascular support. For example, with this simulation, the geometric description provided (e.g., the three-dimensional model) remains unchanged. This is very different from the prior art with which typically in each case, the entire geometric description or the entire three-dimensional model is adapted to a changed vascular geometry in the region of a stenosis. This enables the influence of a therapeutic intervention (e.g., the introduction of the treatment device into the specified length section) to be mathematically quantified and hence estimated precisely. In the present case, this enables the specification of the length section (e.g., however a specification of different length sections) to be used to compare the influence of one or more stenoses and hence the influence of the introduction of the treatment device into the specified length section on the hemodynamic parameter in the distal end region.

A further method act is planning the treatment of the stenosis, where the treatment includes introduction of the treatment device into the specified length section as a function of the simulated value for the hemodynamic parameter. This provides that it is possible in the case of a plurality of stenoses to plan which stenosis is most likely to be treated or for which stenosis treatment will achieve the greatest improvement. It is also possible to plan whether it may be sufficient to treat a sub-segment of the vascular segment, which, for example, only partially includes a diffuse stenosis. Thus, the length section or sections specified for the vascular segment may be specified not only as a function of a position of a stenosis in the vascular segment, but the length of the respective specified length section may also be varied for a specified position in the region of a specific stenosis in order in this way to bring the hemodynamic parameters in the distal end region into a healthy or acceptable value range with the shortest possible treatment device.

This has the advantage that it is possible to predict a future treatment outcome and thus to plan treatment of a stenosis in a quick and simple way. This also entails a non-invasive method that does not require a pressure wire and hence may be implemented in a particularly simple way without invasive measures. It is also possible to consider possible aspects of a future treatment more efficiently after only a preliminary examination after which a geometric description or a three-dimensional model of the vascular segment is already available. For example, it is also possible to determine in advance, in a branch of a multi-branch vessel, in which one vascular segment of a plurality of vascular segments treatment is particularly likely to be successful, so that further, more precise measurement of the hemodynamic parameter (e.g., with a pressure wire) may only be necessary in this vascular segment. Since the simulation relates directly to the derivative c (e.g., is only based on a modified curve of the derivative), this only requires a low amount of computational effort.

Since the described method is based on further analysis of the determined course of the hemodynamic parameter along the vascular segment in order in this way to quantify the individual contributions of one or more respective stenoses for future treatment, the described method does not require geometric description of the vascular segment provided (e.g., the three-dimensional model of the vascular segment provided) to be adapted. Neither are further subsequent calculations of the hemodynamic parameter or of the course of the hemodynamic parameter with, for example, a repeat FFR analysis necessary. Instead, only the course of the hemodynamic parameter along the vascular segment or variables or curves derived therefrom is used. Therefore, the method may also be performed particularly quickly with only low requirements regarding the availability of computing capacity.

In one embodiment, the simulation includes a reduction (e.g., a decrease) of the amount of the derivative c for the specified length section (e.g., in the region of the derivative c corresponding to the region of the vascular segment determined by the length section). For example, herein, the reduction of the derivative may be a reduction of the derivative to zero. For the purposes of this disclosure, this may also be understood to be a reduction of the derivative to substantially zero (e.g., a reduction to maximum 5 percent of the maximum value of the amount of the derivative c). For example, the simulation may also include integration of the derivative c along the length l of the vascular segment (e.g., from the proximal end region to the distal end region of the vascular segment). In this way, the integration of the derivative along the vascular segment from the proximal end region to the distal end region enables the hemodynamic parameter s for the vascular segment with the treatment device introduced virtually therein to be calculated.

This has the advantage that simple modification (e.g., zeroing) of the derivative c for the specified length section with a simple mathematical operation enables the influence of the treatment of the stenosis assigned to the length section with the introduction of the treatment device in the vascular segment in the specified length section to be quantified. The reduction (e.g., the reduction to zero of the derivative c) corresponds to removal of the obstacle (e.g., the stenosis) from the vascular segment or complete compensation of the stenosis.

In an alternative embodiment, the simulation includes integration of the amount of the derivative c over the specified length section. Advantageously, the length section from a proximal end to a distal end of the stenosis is selected, which then determines the overall contribution of the respective stenosis to the course of the hemodynamic parameter s beyond the vascular segment. For example, the integrated amount may be added to a previously determined value for the distal end region of the vascular segment (e.g., calculated or measured value of the hemodynamic parameter). This addition of the integrated amount then corresponds to the virtual introduction of the treatment devices into the specified length section and hence to an improvement of the hemodynamic parameter in the distal end region by the integrated amount. Accordingly, depending upon the respective prefix, an addition may also be understood to be mathematical subtraction with an equivalent effect. Accordingly, the simulated value s may be expressed as $$\hat{s}=s(dE)+\int_{l1}^{l2} c\, dl,$$

where s(dE) is the value of the hemodynamic parameter in the distal end region dE, and l1 and l2 are the end positions of the length section on the length of the vascular segment.

This has the advantage that it is possible to quantify the effect of the treatment with the introduction of the treatment device into the length section with a low amount of computing effort. In a simple way, the corresponding integral for different length sections may be calculated once, and hence, for example, the value thereof may be stored. This also enables simple combinatorial steps to be used automatically to vary an ideal combination of length sections into which one or more treatment devices are to be introduced without it being necessary in each case to calculate a new integral. This again saves on computing capacity and optimizes the therapeutic outcome of the planned treatment.

In a further embodiment, the hemodynamic parameter includes a pressure and/or a pressure gradient and/or a flow velocity and/or a value of a fractional flow reserve of the vascular segment, a FFR value and/or a instantaneous pressure ratio (instantaneous pressure ratio) for the vascular segment and/or a instantaneous wave-free pressure ratio (instantaneous wave free ratio, iFR) for the vascular segment. The corresponding values may be standardized and/or non-standardized values of the hemodynamic parameter.

This has the advantage that the influence of a treatment device introduced into the length section may be described particularly precisely and in a physiologically relevant manner since the variables for the hemodynamic parameter are particularly suitable for a description of the influence of the stenosis.

In an embodiment of the method, the specification and the simulation are performed repeatedly for different length sections, and the planning is performed as a function of the respective simulated values of the hemodynamic parameter for the different length sections. The different length sections may in each case be specified at a same position or same position region (e.g., for an identical stenosis) and varied in length and/or specified with different positions or position regions in each case (e.g., for different stenoses). Accordingly, the length of the length sections specified for different stenoses specified may also be varied (e.g., adapted to the respective stenosis).

This has the advantage that it enables different treatment options with which different stenoses and/or one stenosis may be treated in a plurality of different ways to be quantified and compared with one another. Hence, in a given scenario, it is possible to plan optimum treatment for a plurality of different simulated specified length sections with corresponding simulated values. Herein, the different length sections may be evaluated not only with reference to the respective simulated value for the hemodynamic parameter, but also, for example, based on a length of the length section for the respective simulated value. Shorter length sections may be given preference over longer length sections since the length of the length section may correspond to a length of a treatment device to be introduced. The probability of complications increases with the length of the treatment device, and hence, it may, for example, be more advantageous to plan the treatment with introduction of the treatment device in a shorter length section and accept a less favorable simulated value for the hemodynamic parameter.

In a further embodiment, the planning includes comparison of the at least one simulated value for the hemodynamic parameter with a specified or specifiable limit value, and the treatment is planned as a function of a result of the comparison. For example, when one of the simulated values or the simulated value is lower than the specified limit value, it is possible to dispense with introduction of the treatment device in the length section, for which the simulated value or the one of the simulated values is simulated as treatment or part of the treatment. Herein, the limit value may be specified as a function of the method with which the course of the hemodynamic parameter is determined. For example, for an FFR analysis and an iFR analysis, a different limit value may be selected. Alternatively or supplementarily, the simulated value may be compared with the value determined for the distal end region (e.g., the non-simulated value of the hemodynamic parameter). It may be provided that the introduction of the treatment device into the corresponding length section is dispensed with if the simulated value is not better (e.g., higher) by a specified degree (e.g., by a specified value) than the determined, non-simulated value of the hemodynamic parameter for the distal end region.

This has the advantage that, for the treatment, it is immediately possible in an objectively verifiable way to separate out measures (e.g., the introduction of the treatment device into a corresponding length section) that do not bring about the desired or required degree of improvement. In practice, this also enables the simulation of different treatment combinations since insufficient measures are separated out in a simple way in advance. This is advantageous with an automated or semi-automated method, such as that stipulated in the next embodiment.

In a further embodiment, the specification and/or the simulation and/or the planning is performed automatically by the computing device. For example, a respective length section may be selected by the computing device as one or more length sections for which the amount of the mathematical derivative is higher than a specified value (e.g., higher than zero or higher than 10 percent of the maximum value of the amount of the derivative). The simulation may be automated in a simple way since the simulation only requires a few, well defined, mathematical steps. The planning of the treatment may be automated with the described method since the simulation of the corresponding value of the hemodynamic parameter in the distal end region also provides an evaluation criterion for each of the length sections specified that may be used to evaluate different length sections for the treatment. In addition, herein, a length of the respective method acts may be taken into account as a further evaluation criterion. Preference may be given to shorter length sections over longer length sections.

This has the advantage that the method is performed particularly quickly and simply. This enables a plurality of different treatment options (e.g., a plurality of possible positions or regions into which the respective treatment device may be introduced may be suggested to an operator with a corresponding evaluation during the repeated performance of the specification and the simulation). Hence, there is no need for an operator to perform a laborious qualitative assessment, requiring extensive experience, of the corresponding suitable positions for introduction of a treatment device.

In a further embodiment, the treatment device includes a vascular support (e.g., a stent) and/or a balloon for balloon angioplasty. For example, the treatment includes introduction of the treatment device into the vascular segment (e.g., implantation of the vascular support and/or introduction of the balloon for the balloon angioplasty into the vascular segment). The embodiments described are particularly effective for treating a stenosis with a vascular support.

In a further embodiment, during the planning and, for example, also during the performance of the treatment, a length of the treatment device along a main direction of extent of the treatment device is selected as a function of a length of the specified length section. For example, the length of the treatment device may be selected as the same or substantially equal to the length of the specified length section. Here, 'substantially' may be a deviation of the length of the treatment device from the length of the specified length section of less than 5 percent.

This has the advantage that the specification of the corresponding length section and the simulation of the value for the hemodynamic parameter enable a possible influence of the introduction of the treatment device to be estimated particularly precisely, and hence, the planning for the treatment is improved.

In another embodiment, an end position of the treatment device in the vascular segment into which the treatment device is to be introduced as part of the treatment for the intended use of the treatment device is selected as a function of a corresponding position of the specified length section on the vascular segment. For example, the position of the treatment device in the vascular segment may be, or correspond to, the position of the specified length section on the vascular segment.

This again has the advantage that it enables the outcome (e.g., the influence of the introduction of the treatment device into the vascular segment) to be precisely predicted and quantified.

In a further embodiment, the provision of the geometric description (e.g., the three-dimensional model) is performed based on at least one angiography image. The three-dimensional model may also be provided based on at least one fluoroscopy.

This has the advantage that the hemodynamic parameter may be calculated particularly precisely. With a fluoroscopy (e.g., a real-time angiography image), for example, this enables the influence of the treatment to be predicted particularly precisely.

In an embodiment, visualization of the calculated derivative and/or visualization of the specified length section (e.g., markings of a proximal end and a distal end of the length section on the vascular segment) that may serve as markings for a planned vascular support are displayed superimposed with the at least one angiography image or superimposed with the fluoroscopy on a display device. The visualization may also be superimposed with the fluoroscopy in order to monitor or guide the treatment. The display device may, for example, be a touch-sensitive screen.

This has the advantage that it is possible in a simple way to make the vascular segment or corresponding corrections to the respective markings. For example, markings for a length section into which a vascular support is to be introduced may be particularly easily selected and moved and inspected closely. The superimposition may take place statically or with compensation of a movement of the vascular segment, which may, for example, be caused by a heartbeat or by respiration.

This provides an operator with a particularly simple overview of possible treatments. Herein, the combination of the display of the visualization of the calculated derivative and the angiography image supports an operator in a particularly effective way in the planning of the treatment. Herein, in the case of superimposition with a fluoroscopy, it is also possible to monitor the treatment (e.g., the introduction of the treatment device into the vascular segment since real-time information is available).

In a further embodiment, at least one of the visualizations and the vascular segment are superimposed on the display device in a spatially precise manner. This enables a position of at least one sub-region (e.g., a plurality of sub-regions) of the respective visualization on the display device to correspond to a position of a sub-region of the vascular segment on the display device the properties of which are represented by the visualization in its sub-region or sub-regions. This is possible since the calculated derivative, and hence also the visualization, is based directly on the angiography image or the fluoroscopy and hence the two are automatically registered to one another. This provides that additional registration, such as is or would be necessary for such displays in the prior art, is not required. Therefore, the visualizations and the vascular segment may be superimposed in a particularly simple way requiring little computing capacity. The visualizations may, for example, be stenosis markings, markings for the planned treatment device, or the derivative itself, which is, for example, displayed with color coding.

The described method may also be combined in combination with an invasive method for measuring the hemodynamic parameter (e.g., catheter-based measurement of an FFR value) in order to confirm the need for the treatment and combine the advantage of measuring a real hemodynamic parameter with the flexibility of the virtually calculated hemodynamic parameter values. If a general health value is determined for a patient based on a plurality of parameters, the contribution of the planned treatment simulated may be used to update the health index to a value that the patient is expected to achieve after the corresponding treatment.

One or more of the present embodiments also relate to an examination system for supporting planning (e.g., for planning and/or monitoring of treatment of a stenosis in a vascular segment). For example, the treatment may relate to a stenosis in a vascular segment with a diffuse stenosis and/or a plurality of serial stenoses. The examination system includes an imaging medical apparatus by which a geometric description of the vascular segment (e.g., a three-dimensional model of the vascular segment) may be provided to a computing device of the examination system. The examination system also includes the computing device, which is embodied to determine a course of a hemodynamic parameter s of the vascular segment along the vascular segment based on the geometric description provided (e.g., the model provided). The computing device is further configured to calculate a mathematical derivative $c = ds/dl$ of the hemodynamic parameter s over the length l of the vascular segment along the vessel and to simulate a value of the hemodynamic parameter s in a distal end region of the vascular segment for a treatment device introduced virtually into a specified length section of the vascular segment as a function of the mathematical derivative c. The computing device is, for example, also configured to plan the treatment of the stenosis, which includes introduction of the treatment device into the specified length section of the vascular segment, as a function of the simulated value for the hemodynamic parameter.

Advantages and advantageous embodiments of the examination system correspond to advantages and advantageous embodiments of the described method.

The features and feature combinations mentioned above in the description and the features and feature combinations mentioned below in the description of the figures and/or shown in the figures alone are usable not only in the respectively specified combination, but also in other combinations or alone without departing from the scope of the invention. Hence, embodiments that are not explicitly or explained in the figures, but are derived from and may be generated by separate feature combinations from the explained embodiments may also be considered as encompassed and disclosed by the invention. Hence, embodiments and feature combinations that do not have all the features of an originally formulated independent claim are also to be considered to be disclosed. Moreover, embodiments and feature combinations (e.g., from the above-described embodiments that extend beyond, or deviate from, the feature combinations) described in the back-references in the claims should also be considered to be disclosed.

BRIEF DESCRIPTION OF THE DRAWINGS

In the figures, the same and functionally equivalent elements are given the same reference characters.

DETAILED DESCRIPTION

Figure 1:
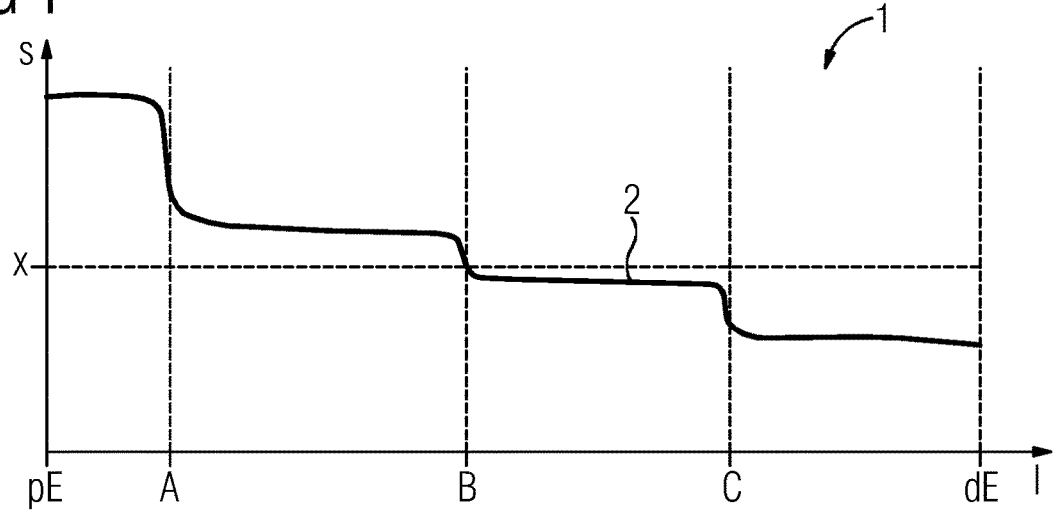
FIG. 1 shows an exemplary course of a hemodynamic parameter s over the length l of an exemplary vascular segment.

FIG. 1 depicts an exemplary course 1 of a hemodynamic parameter s of the vascular segment as a curve 2 over a length l of the vascular segment along the vascular segment. This is, for example, determined by a computing device (e.g., a computer including a processor) based on a geometric description provided (e.g., with reference to a three-dimensional model provided). In the present case, the course of the hemodynamic parameter s is depicted from a proximal end pE of the vascular segment to a distal end dE of the vascular segment.

Since the vascular segment in the example shown has three stenoses at three positions A, B, C, proceeding from the proximal end pE, the value of the hemodynamic parameter s decreases in each case by a different amount at the three positions A, B, C and accordingly reaches a minimum value at the distal end dE. The course of the hemodynamic parameter s between the positions A, B, C of the respective stenoses is substantially constant and then drops sharply at the positions of the stenoses in each case. For example, the hemodynamic parameter s may be a pressure determined along the vascular segment.

In the present case, the value of the hemodynamic parameter s drops as early as at the second position B of the second stenosis to a value below an exemplary limit value x. In the present case, the limit value x is a critical value below which the vascular segment may no longer be classified as healthy. Accordingly, in the present case, treatment of the triple stenosis may be recommended. A qualitative evaluation of the situation is already possible using the curve 2 shown.

Figure 2:
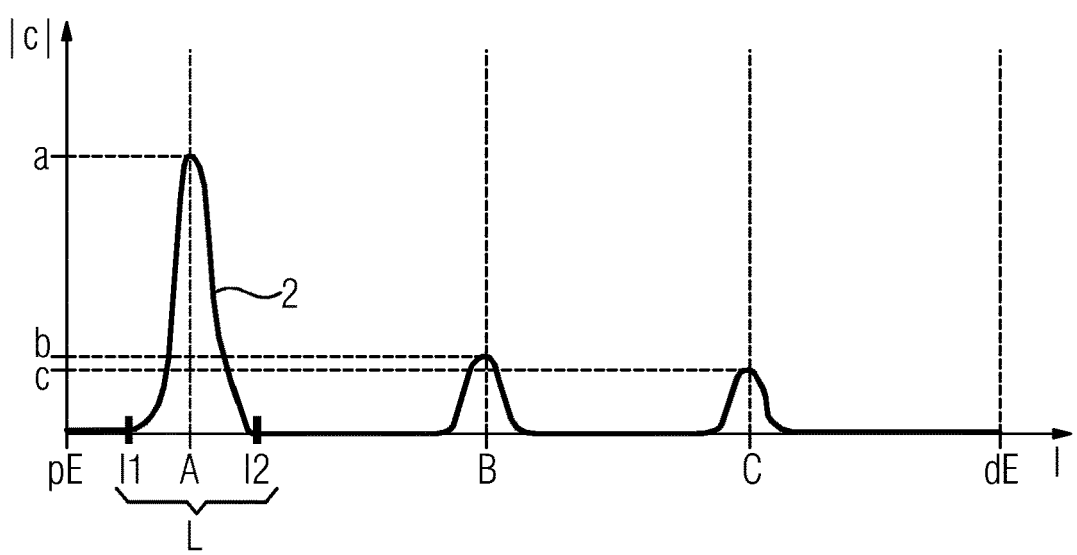
FIG. 2 shows the amount of the mathematical derivative c over the length l for the example in FIG. 1.

FIG. 2 shows the amount of the mathematical derivative c=ds/dl for the course 1 of the hemodynamic parameter s shown in FIG. 1 (FIG. 1) as a curve 2 over the length l of the vascular segment along the vascular segment. The amount of the mathematical derivative reaches respective maxima a, b, c at the three positions A, B, C of the three stenoses. A length section L between two limit positions l1, l2 is specified for the vascular segment for which the influence of a treatment device introduced into the length section L is to be simulated. In the present case, the length section L around the first position A of the first stenosis is selected since the corresponding maximum a is the greatest, and hence, introduction of a treatment device (e.g., a vascular support) at the first position A may have a particularly significant influence on the value of the hemodynamic parameter at the distal end dE of the vascular segment.

In the present case, the limit positions l1, l2 of the length section L are specified such that the first position A is contained in the length section L and, proceeding from the first position A, the limit positions l1, l2 of the length section L are selected as the first positions along the vascular section or the l-axis for which the mathematical derivative c is zero. Alternatively, other positions may be selected for the limit positions l1, l2 (e.g., positions at which the mathematical derivative c reaches a specified different value, such as 5 percent of the value of the assigned maximum (maximum a)). Hence, in the example shown, the length of the length section L is kept as low as possible and, at the same time, maximizes the integral from the first limit position l1 to the second limit position l2 over the amount of the mathematical derivative c. This will be explained in more detail with reference to FIG. 4.

Figure 3:
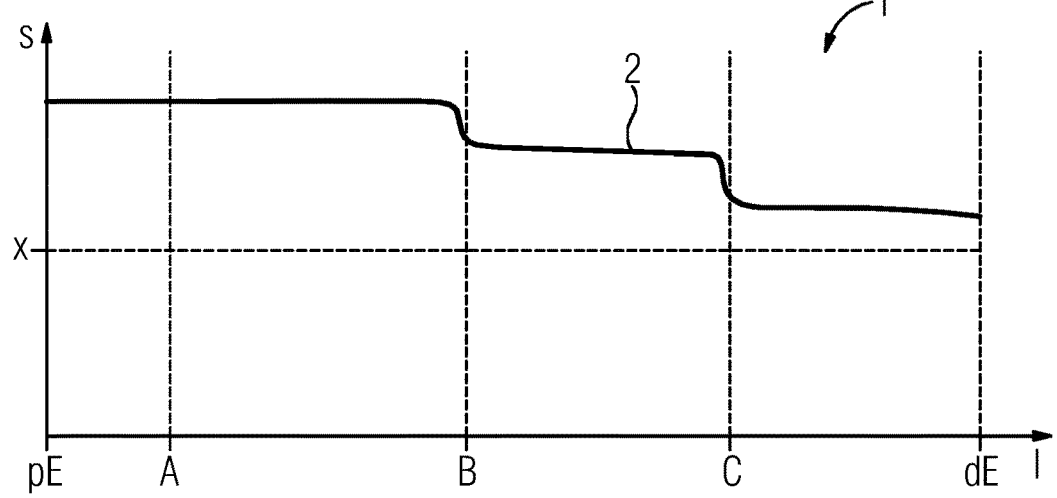
FIG. 3 shows a simulated course of the hemodynamic parameter s over the length l for a treatment device introduced virtually into the vascular segment.

Proceeding from the virtual treatment of the first stenosis A with the virtual introduction of an exemplary treatment device into the length section L described with reference to FIG. 2, FIG. 3 depicts the accordingly resulting simulated course of the hemodynamic parameter s along the vascular segment as a curve 2 over the length l.

In the present case, a value of the hemodynamic parameter s in the distal end region dE of the vascular segment is thus simulated in that a modified version of the mathematical derivative c in FIG. 2 from the proximal end pE to the distal end dE is integrated taking account of the boundary conditions shown in FIG. 1. In the modified version of the derivative c, the curve 2 shown in FIG. 2 in the length section L is replaced by zero since there, due to the virtual treatment of the first stenosis at the first position A, there is no longer any reduction in the hemodynamic parameter s. The integration of the modified version of the derivative may be used to calculate the value of the hemodynamic parameter s for any position along the vascular segment in that the integration is performed from the proximal end pE to the respective position.

In an alternative embodiment, in order to simulate the hemodynamic parameter s in the distal end region, it is also possible, in a first act, to integrate the amount of the derivative c in the length section L from the first limit position l1 to the second limit position l2 and, in a second act, to add the integrated value to the value determined for the hemodynamic parameter s in the distal end region dE. This will be explained in more detail with reference to FIG. 4.

In the present case, the simulated value of the hemodynamic parameter s for one of the two option is greater in the distal end region dE than the limit value x, which indicates that, in the example shown, treatment of the first stenosis at the first position A will be sufficient. In the present case, there is no need for additional risks from additional treatment devices such as, for example, vascular supports implanted at the further stenoses B, C with the corresponding possible medical complications.

Figure 4:
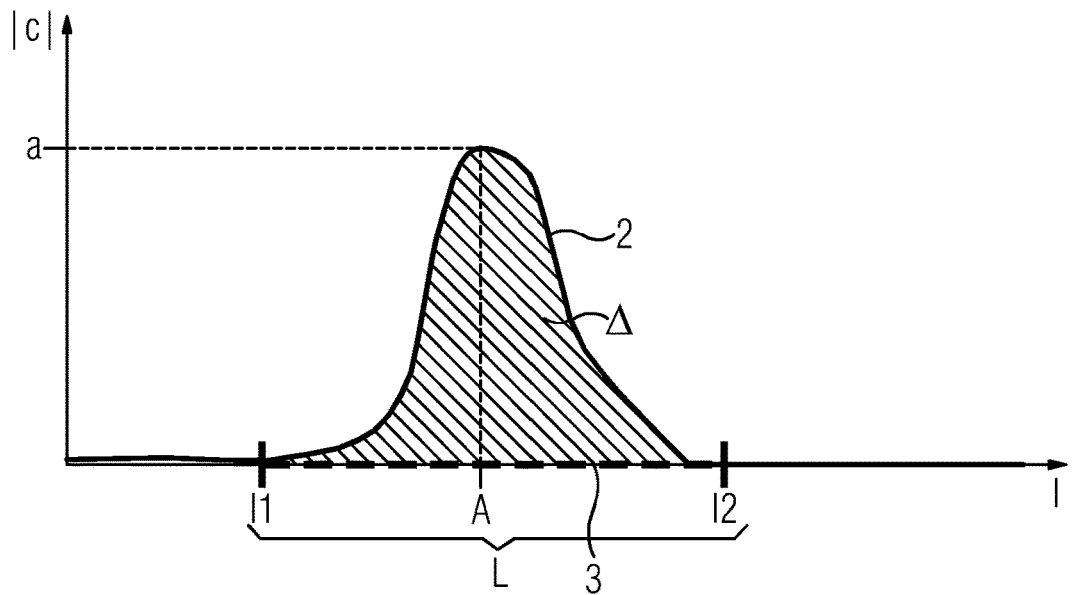
FIG. 4 shows a section of the mathematical derivative c shown in FIG. 2 over the length l with a length section L, into which an exemplary treatment device is introduced.

In FIG. 4, the value of the mathematical derivative c shown in FIG. 2 is depicted as a curve 2 over the length l in a region around the first position A. The first limit position l1 designates the proximal end of the treatment device introduced virtually into the specified length section L of the vascular segment (e.g., the proximal end of a virtual treatment device), and the second limit position l2 designates the distal end of the virtual treatment device. In the present case, the length of the treatment device corresponds to the length of the specified length section L.

Accordingly, the area Δ under the curve 2 of the derivative c between the two limit positions l1, l2 expresses the influence of the vascular segment in the length section L and accordingly, the influence of the first stenosis on the value of the hemodynamic parameter s in the distal end region. In the present case, if the curve 2 in the length section L is replaced by the dashed line 3 (e.g., by zero), on integration of the derivative c from the proximal end region pE to the distal end region dE, there is no area Δ under the curve 2 in the length section L and hence no influence of the first stenosis on the value of the hemodynamic parameter s in the distal end region dE. This corresponds to successful treatment of the first stenosis at the position A.

Since the area Δ quantitatively corresponds to the influence of the first stenosis on the value of the hemodynamic parameter at the distal end dE of the vascular segment, alternatively and with the same effect as the described integration, the value of the integral from the first limit position l1 to the second limit position l2 (e.g., the area A) may be deducted from the value of the hemodynamic parameter determined for the distal end region dE. Hence, this again represents a cure of the first stenosis in the present case such as was planned by the introduction of the treatment device into the length section L.

Figure 5:
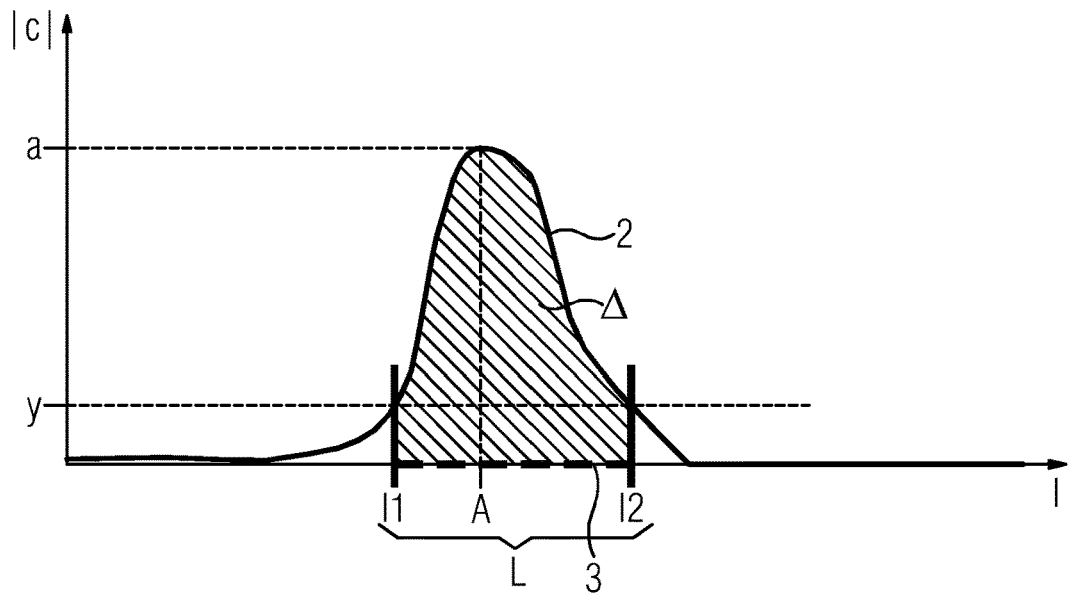
FIG. 5 shows the segment in FIG. 4 with an alternative exemplary length section into which an alternative exemplary treatment device is introduced.

FIG. 5 depicts the segment of the amount of the derivative c depicted in FIG. 4 as a curve 2 over the length l. In the present case, the two limit positions l1, l2 have been varied in order to reduce the length of the length section L. In the present case, the two limit positions l1, l2 have been shifted in the direction of the first position A (e.g., in direction of the maximum a of the curve 2) until the amount of the derivative at the limit positions l1, l2 has adopted a specified value y different from zero. Hence, the area Δ under the curve 2 between the limit positions l1, l2 and the length of the length section L is reduced.

The drawback of the reduced area Δ is the fact that the influence of the first stenosis at position A is not, as in FIG. 4, completely neutralized or treated, but only partially neutralized or treated. However, the advantage of the reduced length of the length section L is the fact that the probability of complications on introduction of the treatment device is reduced since, for example, there is less probability of infection or inflammation. Hence, it is possible to quantify the length of a virtual stent with a quantitative influence on the value of the hemodynamic parameter s in the distal end region dE or on the course of the hemodynamic parameter s visually. At the same time, the quantified influence may be related to a risk of any complications represented by the length of the treatment device and hence considered when planning which treatment of the stenosis will achieve the best risk-benefit balance.

Figure 6:
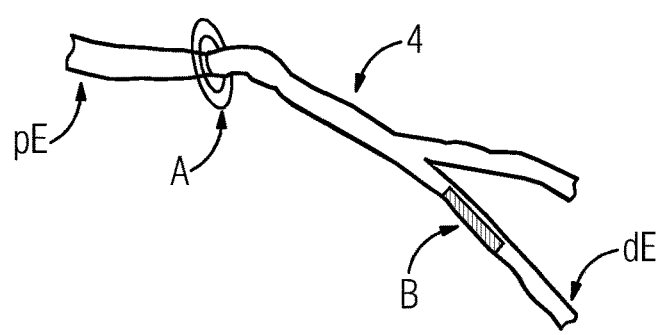
FIG. 6 shows an exemplary depiction of a three-dimensional model of an exemplary vascular segment with a double stenosis.

FIG. 6 depicts, by way of example, a three-dimensional model of an exemplary vascular segment 4 (e.g., a coronary vessel). The model is depicted as representative of another geometric description of the vascular segment, and so, the example may also be explained in a more general form with reference to the geometric representation instead of the three-dimensional model. In the example shown, this is generated from two two-dimensional angiograms with corresponding image processing. In the present case, the image processing acts have a segmentation, a limit detection, a registration of the two angiograms to one another, and a stenosis detection. In the present case, stenoses are detected in the first position A and the second position B of the vascular segment 4. Additionally, in the present case, a hemodynamic parameter (e.g., an iFR value) is also calculated using the three-dimensional model and computer-aided methods with the assumption of a non-hyperemic flow condition. In the example shown, a critical value is obtained for the hemodynamic parameter in the distal end region dE (e.g., an iFR value of 0.77) that may indicate that a hemodynamically relevant stenosis, which hence requires treatment, is present in the vascular segment 4.

Figure 7:
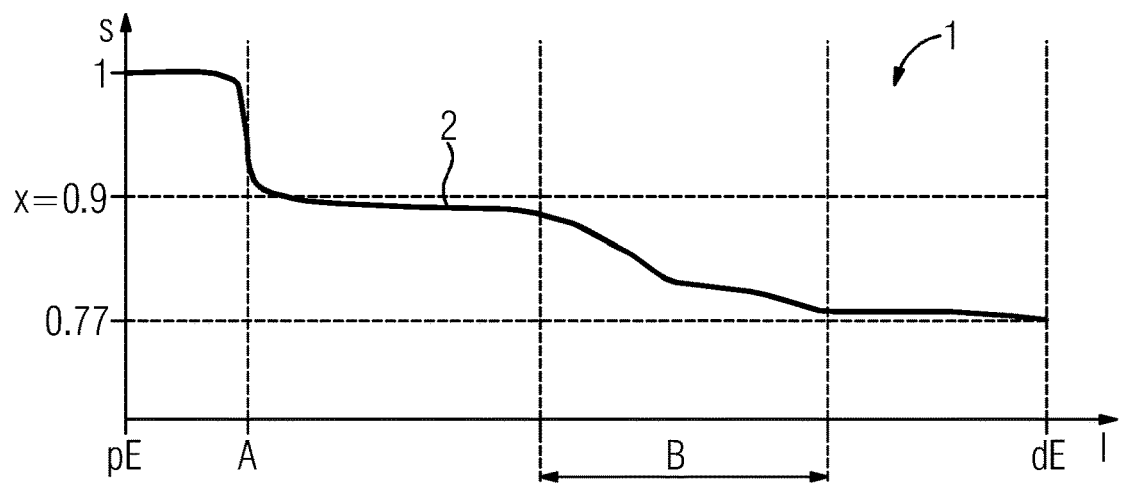
FIG. 7 shows the exemplary course of the hemodynamic parameter s over the length l for the vascular segment in FIG. 6.

FIG. 7 depicts the course 1 of the hemodynamic parameter s as a curve 2 over the length l along the vascular segment 4. In the present case, the hemodynamic parameter s is a standardized hemodynamic parameter (e.g., the iFR value). The course 1 thereof from the proximal end pE to the distal end dE may be an indication that two stenoses are present in the present case (e.g., at a first sharp drop in the curve 2 at the first position A and a further drop in the hemodynamic parameter in a second, poorly demarcated, position B). The first stenosis at the first position A is thus a clearly localized stenosis, while, in the present case, the second stenosis at the second, not clearly demarcated position B is a diffuse stenosis. The question that is now raised as part of the treatment is whether it is necessary to treat both stenoses or whether it is sufficient to treat one of the two stenoses and, if so, which one of the two. A lower number of interventions and implanted treatment devices such as, for example, vascular supports reduces not only the amount of surgery but also any future health risks for the patient.

Figure 8:
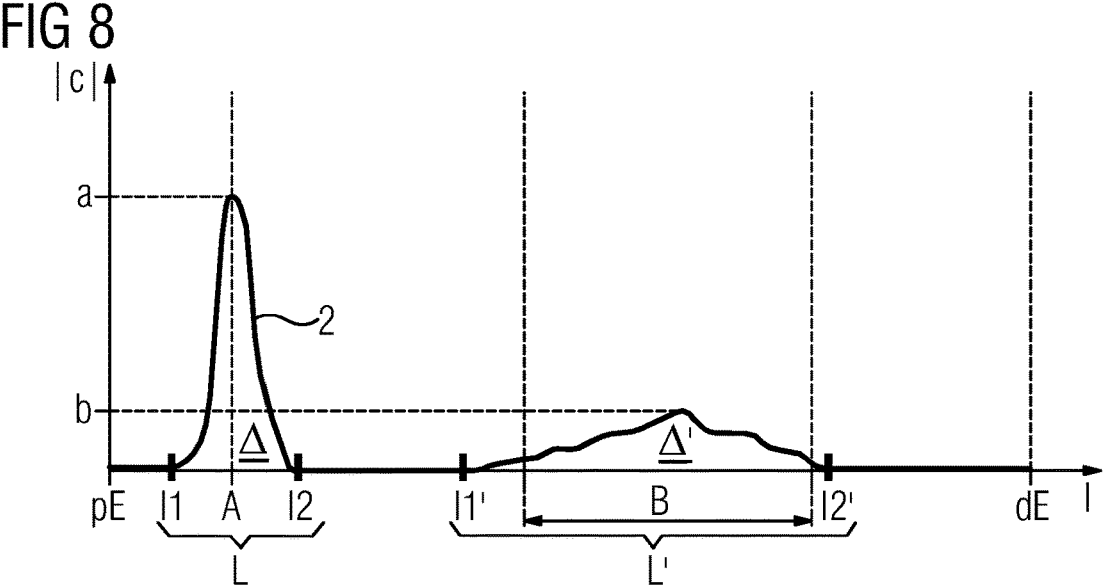
FIG. 8 shows the amount of the mathematical derivative c of the hemodynamic parameter s over the length l in FIG. 7.

In FIG. 8, the amount of the mathematical derivative c of the course 1 shown in FIG. 7 is plotted as a curve 2 over the length l. In the present case, two length sections L, L' are selected, in each case containing the assigned position A, B in order to simulate the influence of respective treatment device introduced into the length sections L, L'.

Accordingly, respective limit positions l1, l2 or l1', l2' are selected for the length sections L or L' at which positions the derivative c from the proximal end pE before or after the corresponding maxima a, b at the positions A, B is still zero or drops again to zero. Accordingly, the areas Δ, Δ' under the curve 2 in the length sections L, L' determine the degree to which the stenoses in position A or B contribute to the value of the hemodynamic parameter s at the distal end.

In the example shown, a value of 0.15 is obtained for the first area Δ in the first length section L at position A, and a value of 0.11 is obtained for the second area Δ' in the second length section L' at position B. The stenosis at the first position A thus has a greater influence on the hemodynamic parameter s than the stenosis at the second position B. Accordingly, as expected, the respective introduction of a treatment device such as a stent increases the iFR value from 0.77 to 0.92 for a stent in the first length section L and from 0.77 by 11 to 0.88 for a stent in the second length section L'. Since, for example, a critical limit of 0.9 is generally recognized for the hemodynamic parameter (e.g., the iFR value), in the present case, the introduction of a treatment device into the second length section L' does not achieve a sufficient improvement, while the introduction of a treatment device into the first length region L does. The treatment of the stenosis in the first position A also uses a shorter treatment device that has further advantages. It may also be advantageous to simulate the hemodynamic parameter s not only in the distal end region dE, but also along the course 1 of the vascular segment 4. This is also depicted in FIG. 3 and will be explained below accordingly with reference to FIG. 9.

Figure 9:
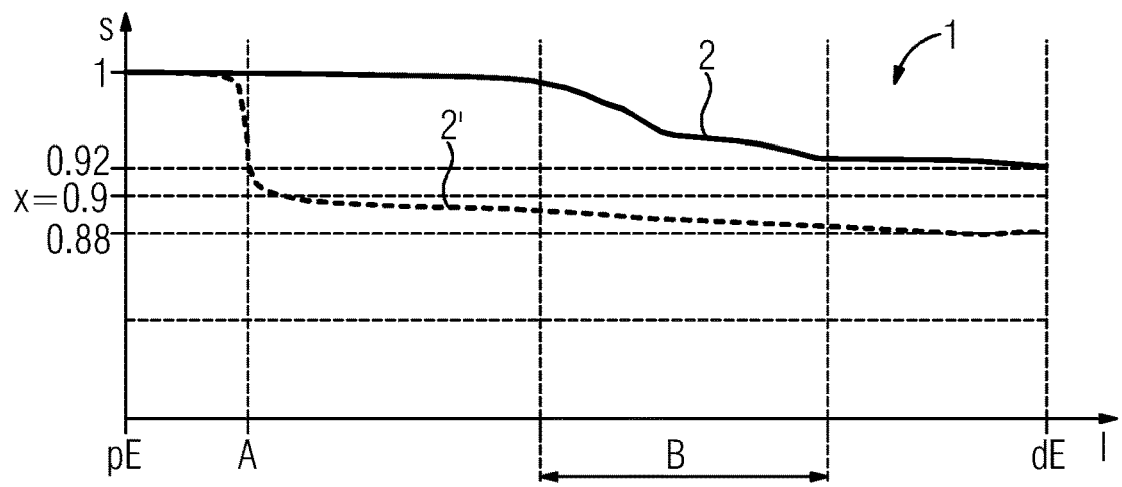
FIG. 9 shows two simulated exemplary courses of the hemodynamic parameter s over the length l for the vascular segment in FIG. 6 for different treatment devices introduced into the vascular segment by way of example.

FIG. 9 shows the course 1 of the hemodynamic parameter s over the length l from the proximal end pE to the distal end dE of the vascular segment 4 based on a first curve 2 and a second curve 2'. The first curve 2 corresponds to an integral over the amount of the derivative shown in FIG. 8, which has been replaced by zero in the first length section L. Accordingly, the second curve 2' shows the course 1 of the hemodynamic parameter s, which is simulated based on the amount of the derivative shown in FIG. 8, with which the derivative c in the second length section L' is replaced by zero. As a result, the first curve 2 does not drop at the first position A, but only at the second position B; the second curve 2' drops sharply at the first position A and remains unchanged over the second region or the second position B. This method has the advantage that a person performing the treatment (e.g., a doctor) not only obtains an end value, such as, for example, 0.88 or 0.92, but may also obtain a more accurate and comprehensive idea of the situation in the vascular element 4.

Figure 10:
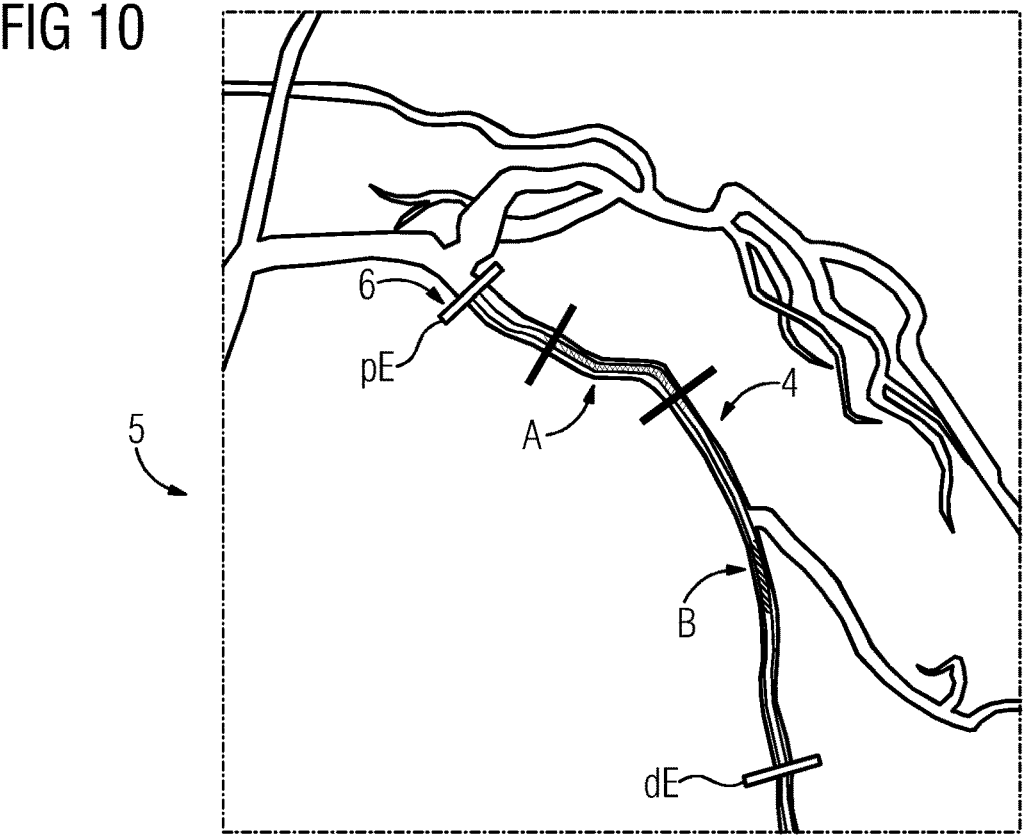
FIG. 10 shows an exemplary visualization of the course of the mathematical derivative c over the length, which is superimposed with the depiction of the vascular segment in FIG. 6.

FIG. 10 depicts an exemplary visualization 6 of the derivative c superimposed with an angiography image, based on which the model in FIG. 6 is calculated in the present case. Such a superimposition may also be depicted on a display device. For example, a middle line of the vascular segment 4 from the proximal end pE to the distal end dE corresponding to a local amount of the derivative c is locally colored. For example, regions with a large change in the hemodynamic parameter s (e.g., a derivative with a high value) may be colored red, regions with a smaller change may be colored yellow or orange, and regions in which the hemodynamic parameter does not change and accordingly the derivative c is zero or close to zero may be marked with green. In the depictions, the colors are represented by different types of hatching. In the present case, a non-hatched middle line represents a green middle line, a middle line with single hatching represents a yellow or orange middle line, and a middle line with double hatching represents a red middle line. This method of color representation is also selected in FIG. 11 for the middle line of the vascular segment 4. The proximal end pE and the distal end of the vessel 4 may also be marked.

This superimposition has the advantage that the position of the vascular segment 4 and the degree of a critical change to the hemodynamic parameter s is particularly clear to an operator. Since the calculations and hence also the course of the derivative c were determined based on the model, which, in the present case, was produced from the displayed angiography image, there is also already a clear spatial relationship between the simulated data or the calculated derivative and the vascular segment 4. Hence, additional registration or like is not necessary, and this saves a large amount of time and computing capacity.

Figure 11:
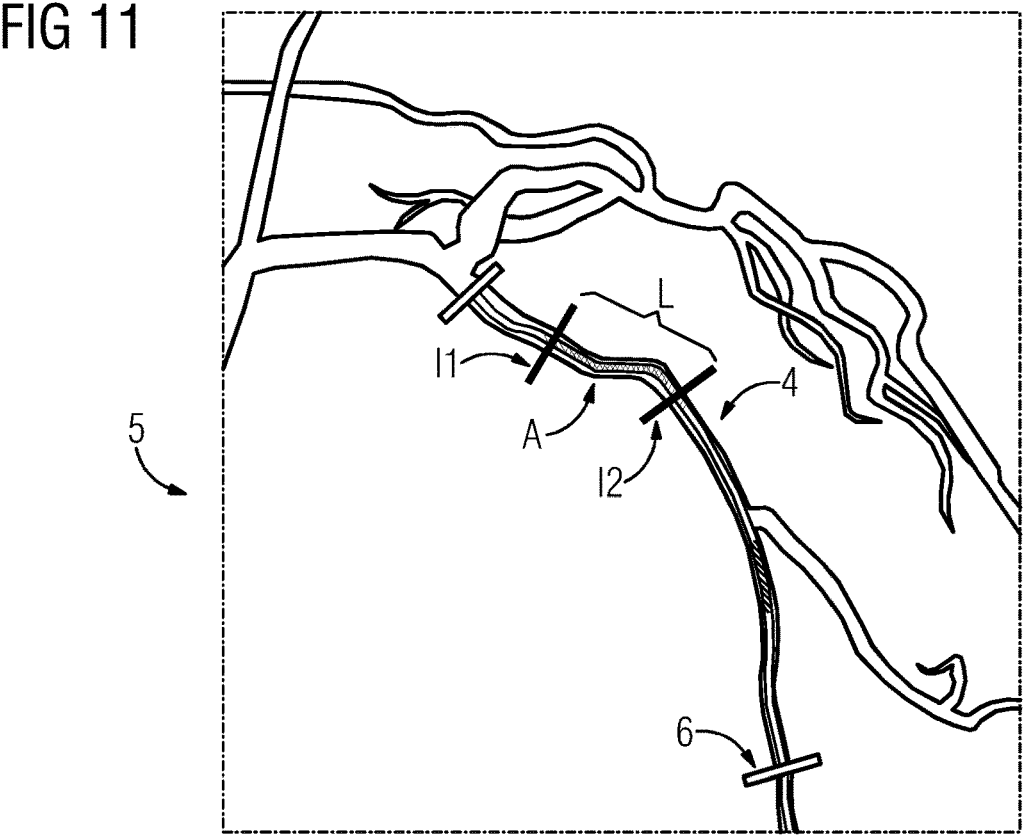
FIG. 11 shows a second exemplary visualization of the mathematical derivative c over the length l, which is superimposed with the depiction of the vascular segment in FIG. 6.

Hence, such a visualization 6 is suitable for therapy guidance (e.g., for monitoring treatment with which on a fluoroscopy as an angiography, the treatment device (a stent) is introduced into the vascular segment 4 under visual control on the fluoroscopy (the angiography) displayed to the operator). As shown in FIG. 11, additional markings may be superimposed with the angiography as a further visualization 7 of the specified length section L. This may also be useful in order, for example, to show an operator a depiction of the recommended position of the length section L on the vascular segment 4.

Figure 12:
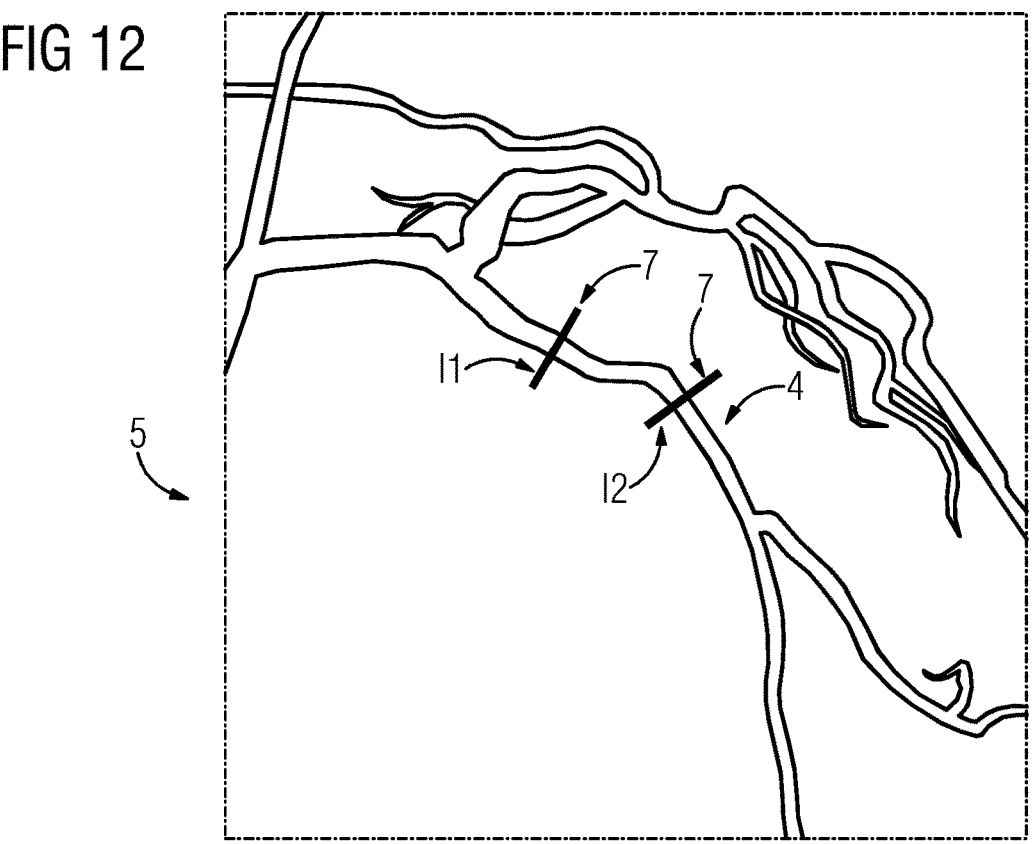
FIG. 12 shows an exemplary visualization of the specified length section, which is superimposed with the depiction of the vascular segment in FIG. 6.

However, as depicted in FIG. 12, for better therapy guidance, only the further visualization 7 of the specified length section L may be provided (e.g., by marking the corresponding limit positions l1, l2 on the angiography). Hence, the actual vascular segment 4 is not masked by the visualization 6 of the calculated derivative on the angiography, thus enabling better monitoring.

Figure 13:
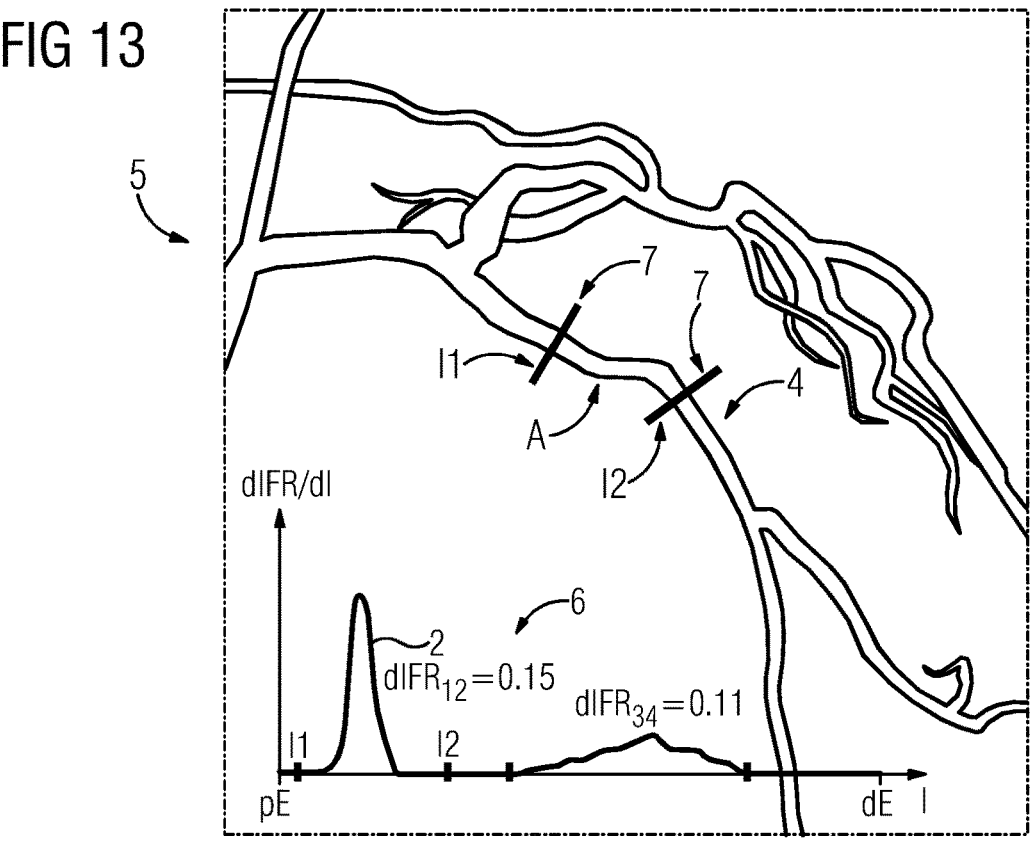
FIG. 13 shows a further exemplary superimposition of a visualization of the specified length section and the mathematical derivative on the depiction in FIG. 6.

However, alternatively, the visualization 6 of the calculated derivative may also be superimposed with the angiography 5 in the form of a curve that does not mask the vascular segment 4, such as is depicted, for example, in FIG. 13. Markings corresponding to one another (e.g., the markings of the limit positions l1, l2) may be unambiguously marked in each case, thus enabling an observer to automatically assign the corresponding features on the curve 2 to the further visualization 7, which is superimposed directly with the vascular segment 4.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for planning treatment of a selected stenosis in a vascular segment, the method comprising:
   providing a geometric description of the vascular segment to a computer, the vascular segment including at least two stenoses;
   determining, by the computer, a course of a hemodynamic parameter of the vascular segment along the vascular segment based on the provided geometric description;
   calculating, by the computer, a mathematical derivative of the hemodynamic parameter over a length of the vascular segment along the vascular segment;
   specifying at least two length sections for the vascular segment, each length section of the at least two length sections including a stenosis of the at least two stenoses;
   selecting only one of the at least two specified length sections for the planned treatment, wherein the stenosis included in the selected one length section has a greatest influence of the at least two length sections on a hemodynamic parameter in a distal end region of the vascular segment;
   simulating a value of the hemodynamic parameter in the distal end region of the vascular segment for a treatment device introduced virtually into the selected one length section as a function of the calculated mathematical derivative of the hemodynamic parameter over the length of the vascular segment; and
   planning the treatment of the stenosis including an introduction of the treatment device into the selected one length section as a function of the simulated value for the hemodynamic parameter.

2. The method of claim 1, wherein simulating the value of the hemodynamic parameter comprises reducing an amount of the calculated mathematical derivative for the selected length section of the calculated mathematical derivative.

3. The method of claim 2, wherein reducing the amount of the derivative for the selected length section of the calculated mathematical derivative comprises reducing the calculated mathematical derivative to zero and integrating the calculated mathematical derivative.

4. The method of claim 1, wherein simulating the value of the hemodynamic parameter comprises integrating an amount of the calculated mathematical derivative over the selected length section and adding the integrated amount to a previously determined value of the hemodynamic parameter for the distal end region.

5. The method of claim 1, wherein the hemodynamic parameter comprises a pressure, a pressure gradient, a flow velocity, a value of a fractional flow reserve of the vascular segment, an instantaneous pressure ratio for the vascular segment, an instantaneous wave-free pressure ratio for the vascular segment, or any combination thereof.

6. The method of claim 1, wherein the specifying and the simulating are performed repeatedly for different length sections, and the planning is performed as a function of the respective simulated values for the different length sections.

7. The method of claim 1, wherein the planning comprises:
   comparing the at least one simulated value for the hemodynamic parameter with a specified limit value;
   planning the treatment as a function of a result of the comparing; and
   rejecting introduction of the treatment devices into the selected length section for which the one simulated value is simulated as treatment when one of the simulated values is lower than the specified limit value.

8. The method of claim 1, wherein the specifying, the simulating, the planning, or any combination thereof is performed automatically by the computer.

9. The method of claim 1, wherein the treatment device comprises a vascular support, a balloon for balloon angioplasty, or the vascular support and the balloon.

10. The method of claim 1, wherein a length of the treatment device along a main direction of extent of the treatment device is selected as a function of a length of the selected length section.

11. The method of claim 10, wherein the length of the treatment device is selected as equal to the length of the selected length section.

12. The method of claim 1, wherein an end position of the treatment device in the vascular segment into which the treatment device is to be introduced as part of the treatment is selected as a function of a position of the selected length section on the vascular segment.

13. The method of claim 12, wherein the end position of the treatment device in the vascular segment is the position of the selected length section on the vascular segment.

14. The method of claim 1, wherein providing the geometric description comprises providing the geometric description based on at least one angiography image.

15. The method of claim 14, further comprising displaying, by a display device, a visualization of the calculated mathematical derivative, a visualization of the selected length section, or the visualization of the calculated mathematical derivative and the visualization of the selected length section superimposed with the at least one angiography image.

16. The method of claim 15, wherein the at least one angiography image comprises a fluoroscopy.

17. The method of claim 15, wherein the visualization of the calculated mathematical derivative, the visualization of the selected length section, or the visualization of the calculated mathematical derivative and the visualization of the selected length section, and the vascular segment are superimposed on the display device in a spatially precise manner.

18. An examination system for supporting planning of treatment of a selected stenosis in a vascular segment, the examination system comprising:
   a computer; and
   an imaging medical device by which a geometric description of the vascular segment is providable to the computer, the vascular segment including at least two stenoses,
   wherein the computer is configured to:
      determine a course of a hemodynamic parameter of the vascular segment along the vascular segment based on the geometric description provided;
      calculate a mathematical derivative of the hemodynamic parameter over a length of the vascular segment along the vascular segment;
      specify at least two length sections for the vascular segment, each length section of the at least two length sections including a stenosis of the at least two stenoses;
      select only one of the at least two specified length sections for the planned treatment, wherein the stenosis included in the selected one length section has a greatest influence of the at least two length sections on a hemodynamic parameter in a distal end region of the vascular segment; and
      simulate a value of the hemodynamic parameter in the distal end region of the vascular segment for a treatment device introduced virtually into the selected length section of the vascular segment as a function of the calculated mathematical derivative of the hemodynamic parameter over the length of the vascular segment.

19. The method of claim 1, wherein selecting the one specified length section for the planned treatment comprises quantifying an influence of each stenosis of the at least two stenoses contained in each specified length section of the at least two length sections on the hemodynamic parameter in the distal end region of the vascular segment with the calculated mathematical derivative of the hemodynamic parameter over the length of the vascular segment.

* * * * *